United States Patent
Harvey et al.

(10) Patent No.: US 10,981,846 B1
(45) Date of Patent: Apr. 20, 2021

(54) PRODUCING CYCLIC FUELS FROM CONJUGATED DIENE

(71) Applicants: The United States of America, as represented by the Secretary of the Navy, Arlington, VA (US); The Trustees of Princeton University, Princeton, NJ (US)

(72) Inventors: Benjamin G. Harvey, Ridgecrest, CA (US); Kyle E. Rosenkoetter, Ridgecrest, CA (US); Paul Chirik, Princeton, NJ (US); C. Rose Kennedy, Princeton, NJ (US)

(73) Assignees: The United States of America, as Represented by the Secretary of the Navy, Washington, DC (US); The Trustees of Princeton University, Princeton, NJ (US)

( * ) Notice: Subject to any disclaimer, the term of this patent is extended or adjusted under 35 U.S.C. 154(b) by 68 days.

(21) Appl. No.: 16/542,547

(22) Filed: Aug. 16, 2019

(51) Int. Cl.
*C07C 5/03* (2006.01)
*B01J 31/02* (2006.01)
*C07C 2/46* (2006.01)
*C10L 1/16* (2006.01)
*C10L 1/04* (2006.01)
*C07C 7/04* (2006.01)
*C07C 2/44* (2006.01)
*C07C 13/26* (2006.01)

(52) U.S. Cl.
CPC .............. *C07C 5/03* (2013.01); *B01J 31/0241* (2013.01); *C07C 2/44* (2013.01); *C07C 2/46* (2013.01); *C07C 2/465* (2013.01); *C07C 7/04* (2013.01); *C10L 1/04* (2013.01); *C10L 1/1608* (2013.01); *B01J 2231/64* (2013.01); *B01J 2531/821* (2013.01); *B01J 2531/824* (2013.01); *B01J 2531/828* (2013.01); *B01J 2531/847* (2013.01); *C07C 13/26* (2013.01); *C07C 2531/02* (2013.01)

(58) Field of Classification Search
CPC .... C07C 5/03; C07C 2/44; C07C 2/46; C07C 7/04; C07C 2/465; C07C 13/26; C07C 2531/02; B01J 31/0241; B01J 2531/847; B01J 2231/64; B01J 2531/828; B01J 2531/824; B01J 2531/821; C10L 1/04; C10L 1/1608
See application file for complete search history.

(56) References Cited

U.S. PATENT DOCUMENTS

2012/0157725 A1* 6/2012 McAuliffe ........... B01J 31/2273
585/16
2019/0374932 A1* 12/2019 Pampaloni ............... B01J 31/20

* cited by examiner

*Primary Examiner* — Ali Z Fadhel
(74) *Attorney, Agent, or Firm* — Naval Air Warfare Center Weapons Division; Matthew D. Pangallo

(57) ABSTRACT

A method for making a fuel includes reacting a conjugated diene or a mixture of conjugated dienes with a catalyst selected from the group consisting of a low valent iron catalyst stabilized with a pyridineimine ligand, an iron precatalyst coordinated to the pyridineimine ligand that is activated with a reducing agent, a low oxidation state Fe complex stabilized with a pyridineimine ligand and a coordinating ligand, and combinations thereof, thereby forming a substituted cyclooctadiene. The substituted cyclooctadiene is then hydrogenated, thereby forming cyclooctane fuel.

20 Claims, 10 Drawing Sheets isoprene → 1,6-dimethyl-1,4-cyclooctadiene (DMCOD) → 1,4-dimethylcyclooctane (DMCO)

US 10,981,846 B1

PRODUCING CYCLIC FUELS FROM CONJUGATED DIENE

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

Fuel precursors can be chemically produced from petroleum and bio-based sources or obtained from naturally occurring crude oil sources. When producing fuel from crude oil sources, a complex mixture of hydrocarbons is added to a distillation column with a temperature gradient to separate the molecules based on their molecular weight and volatility. Isolation of a well-defined distillation cut allows for the production of various fuel blends with properties suitable for use in specific applications. For example, jet fuel may contain a mixture of hydrocarbons having between 9 to 14 carbon atoms in each molecule.

BRIEF DESCRIPTION OF THE DRAWINGS

Features and advantages of examples of the present disclosure will be apparent by reference to the following detailed description and drawings, in which like reference numerals correspond to similar, but in some instances not identical, components. Reference numerals or features having a previously described function may or may not be described in connection with other drawings in which they appear.

DETAILED DESCRIPTION

Currently, methods of producing fuel from sustainable sources include several drawbacks that hinder the ability to mass-produce the fuel. For example, some of these methods are based on a limited sustainable source, are non-selective for a desired fuel product, too complex to allow for production at an industrial scale, are too expensive, or a combination of these issues. Furthermore, some biofuels, such as synthetic paraffinic kerosene (SPK) derived from ethanol and butanol, do not meet the required specifications for drop-in jet fuels. In particular, the low density of these fuels negatively affects their volumetric net heats of combustion.

The method described herein for making a fuel includes a two-step process selective for the preparation of a jet fuel surrogate, and in some instances, diesel fuel. Moreover, the method can be conducted at low temperatures and pressures using a catalyst based on an earth abundant metal with a high turnover number, which reduces the cost to mass-produce the fuel. As a result, the method provides a high throughput, practical route to high performance fuels from bio-based, sustainable sources.

In addition, the fuel produced herein has a higher gravimetric and volumetric net heat of combustion, a higher density, and a higher flash point compared to conventional jet fuel (e.g., Jet-A, Jet-A1, JP-5, F-24, or JP-8 fuel). The fuel also has a lower viscosity and freezing point compared to conventional jet fuel. As a result, the fuel described herein qualifies as a drop-in fuel that may be blended with either conventional or bio-based jet fuels to improve fuel performance, and decrease the operational costs of aircraft.

The method for making a fuel includes reacting a conjugated diene or a mixture of conjugated dienes with a catalyst selected from the group consisting of a low valent iron catalyst stabilized with a pyridineimine ligand, an iron precatalyst coordinated to the pyridineimine ligand that is activated with a reducing agent, a low oxidation state Fe complex stabilized with a pyridineimine ligand and a coordinating ligand, and combinations thereof, thereby forming a substituted cyclooctadiene. The substituted cyclooctadiene is then hydrogenated, thereby forming cyclooctane fuel.

Figure 1:
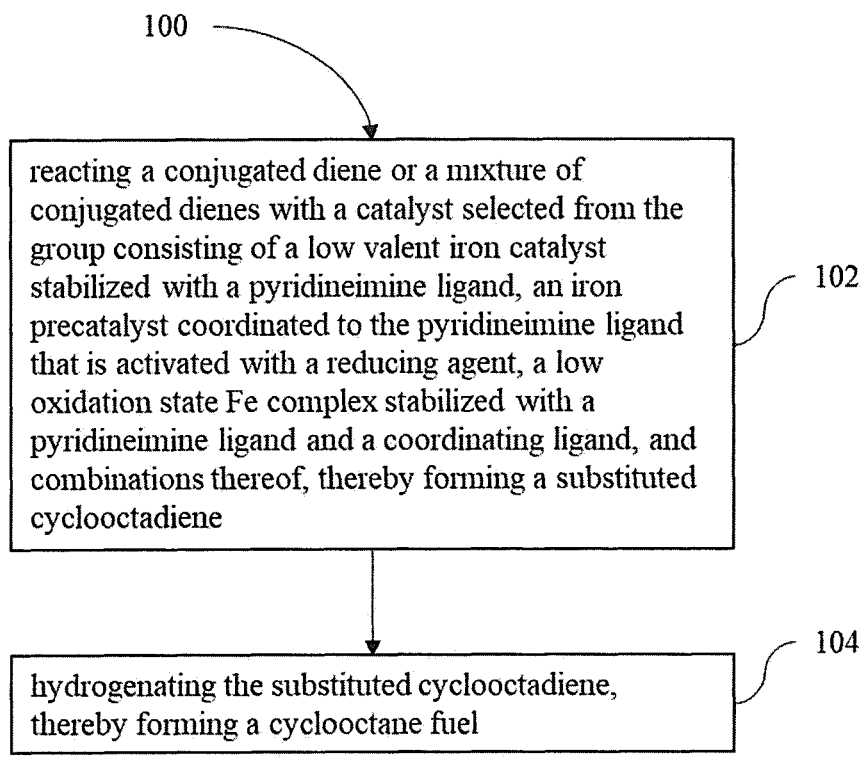
FIG. 1 is a flow diagram illustrating an example of a method for making a fuel described herein.

Referring now to FIG. 1, the method 100 for making a fuel includes step 102 of reacting a conjugated diene or a mixture of conjugated dienes with a catalyst selected from the group consisting of a low valent iron catalyst stabilized with a pyridineimine ligand, an iron precatalyst coordinated to the pyridineimine ligand that is activated with a reducing agent, a low oxidation state Fe complex stabilized with a pyridineimine ligand and a coordinating ligand, and combinations thereof, thereby forming a substituted cyclooctadiene. This reaction forms a fuel precursor that can be converted to a final product in the subsequent step. In an example, the ratio of the conjugated diene or the mixture of conjugated dienes to the catalyst present in the reaction is from about 100:1 to about 1,000,000:1. In a specific example, the ratio of conjugated dienes or mixture of conjugated dienes to the catalyst present in the reaction is 4,000:1. In an example, this reaction occurs at a temperature ranging from about −80° C. to about 100° C. for a time ranging from about 1 hour to about 48 hours. In another example, the reaction occurs at a temperature ranging from about 0° C. to about 40° C. The reaction is conducted under an inert atmosphere (e.g., argon, nitrogen). In some examples, the reaction is performed using the conjugated diene or mixture of conjugated dienes as both the solvent and reactant without any additional solvent in the reaction.

The conjugated diene or mixture of conjugated dienes (e.g., isoprene) is used as a precursor in method 100 since it can be produced from sustainable sources. However, the conjugated dienes can also be produced from petroleum-based sources as well. In an example, the conjugated dienes or mixture of conjugated dienes includes a number of carbons ranging from about 4 carbons to about 20 carbons for each molecule. Some examples of the conjugated dienes include butadiene, pentadienes, hexadienes, heptadienes, octadienes, or combinations thereof. In some examples, the conjugated dienes or mixture of conjugated dienes listed herein are used as both a solvent and a reactant (i.e. a diene substrate) without any additional solvent in the reaction. The conjugated dienes may be produced using any known method. For example, isoprene can be produced from methylbutenols (e.g., 3-methyl-3-butene-1-ol) via dehydration or by using fermentation. Another example includes producing butadiene from 2,3-butanediol or another bio-based alcohol.

The catalyst allows the fuel in the method 100 to be produced in two steps. The catalyst may be a low valent iron catalyst stabilized with a pyridineimine ligand (RPI). An example of the precatalyst structure is shown in the general structure (I) below:

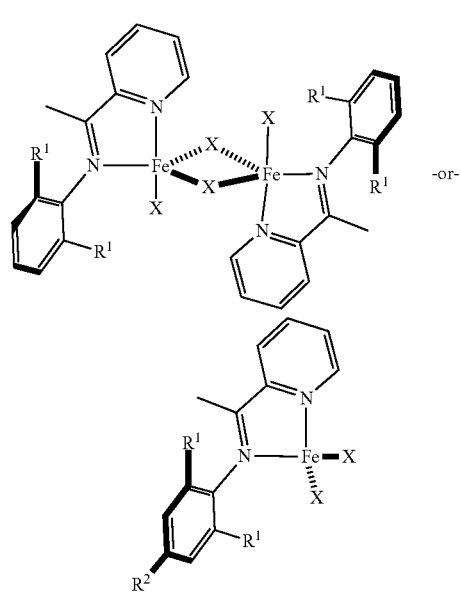

$R^1, R^2$ = Me, Et, i-Pr, H; X = Cl, Br

The precatalyst (I) may be activated by a reducing agent to form the catalyst. In one example, the catalyst may be activated by treating [(RPI)FeCl$_2$]$_2$ with Mg(C$_4$H$_6$).2THF and COD (1,5-cyclooctadiene) in thawing Et$_2$O over the course of 10 minutes to 20 minutes. In another example, the catalyst may be activated by treating [(RPI)FeCl$_2$]$_2$ with MeMgCl in an inert environment for several minutes. In an example, the catalyst facilitates a monomer conversion of about 92%. For example, the catalyst has a turnover number (TON) ranging from about 100 to about 1,000,000. In another example, when the ratio of the monomers (i.e., conjugated dienes) to the catalyst is 4000:1, the TON number is about 3680.

The catalysts may be heterogeneous or homogeneous. The heterogeneous catalyst may be a metal catalyst bound to a support material where the support material is an inorganic material or a polymeric material. Some specific examples of pyridineimine ligands used in the catalyst represented by the general structure (I) above include N-(2,6-dimethylphenyl)-1-(pyridin-2-yl)ethan-1-imine, N-(2,6-diethylphenyl)-1-(pyridin-2-yl)ethan-1-imine, N-(2,6-diisopropylphenyl)-1-(pyridin-2-yl)ethan-1-imine, N-(2,4,6-triimethylphenyl)-1-(pyridin-2-yl)ethan-1-imine, and combinations thereof. In another example, the catalyst may be a precatalyst, such as [(RPI)FeX$_2$]n where RPI is a pyridineimine, X is Cl, Br, or I, n is 1 or 2, and the precatalyst is activated in situ with reducing agents. Examples of reducing agents include MeMgCl, Mg(C$_4$H$_6$).THF, Mg(0), Mn(0), or NaBHEt$_3$. In yet another example, the catalyst may be a low oxidation state Fe catalyst that is stabilized with a pyridineimine ligand and a coordinating ligand, such as 1,5-cyclooctadiene or norbornadiene.

After the reaction is complete, the product from step 102 can be isolated directly from the reaction mixture using any known methods. For example, the product can be isolated using vacuum distillation. The conversions may be equal to or less than 100% conversion of the conjugated diene or mixture of conjugated dienes to the products (i.e., cyclooctadiene). The products can be cyclooctadienes with the following structure (II)

Figure 2:
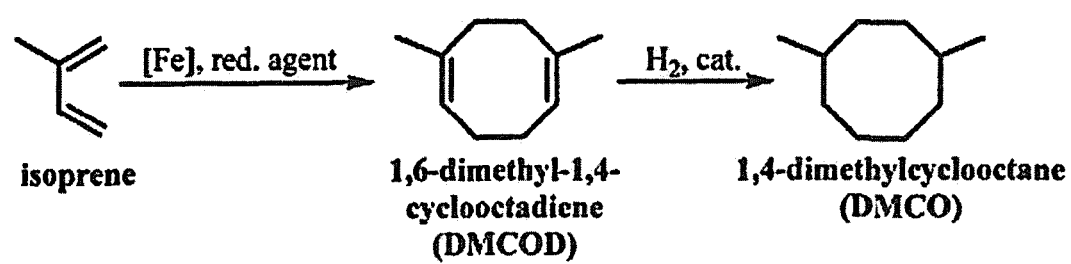
FIG. 2 is a scheme illustrating an example of a method for making a fuel described herein.

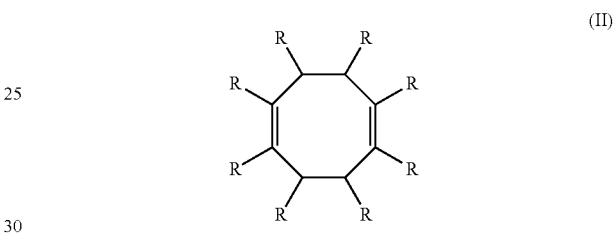

where the R groups are independently a hydrogen atom or an alkyl group. In an example, the product of step 102 may be 1,6-dimethyl-1,5-cyclooctadiene. In another example, step 102 is shown in FIG. 2. Isoprene is reacted with an Fe-based catalyst and a reducing agent to form 1,6-dimethyl-1,4-cyclooctadiene (1,6-DMCOD).

Referring back to FIG. 1, method 100 includes another step 104, which entails hydrogenating the cyclooctadiene, thereby forming a cyclooctane fuel. This reaction is conducted at a temperature ranging from about 20° C. to about 200° C. and a pressure ranging from about 1 atm to about 500 atm. The reaction may occur for a time ranging from about 1 hour to about 24 hours. In some examples, the reaction in step 104 uses a heterogeneous catalyst, including a heterogeneous catalyst based on Ni, Pd, Pt, or Ru. In other examples, a homogeneous catalyst based on Fe or Ni may be used. A polar solvent may be used to increase the rate and degree of conversion. Some examples of the polar solvent include acetic acid, methanol, ethanol, and combinations thereof.

To obtain the cyclooctane fuel in step 104, after the reaction is complete, the fuel is purified to remove the catalyst. Any known purification methods can be used to remove the catalysts. For example, when a heterogeneous catalyst is used, the catalyst may be removed by filtration followed by distillation to purify the fuel. The heterogeneous catalyst may then be recycled or reused again in a subsequent reaction using the method herein to produce more cyclooctane fuel. In another example, when a homogenous catalyst is used, the product may be removed by low temperature vacuum distillation and more substrate (i.e., the conjugated diene(s)) may be added to the homogeneous catalysts in a subsequent reaction to produce more cyclooctane fuel using the method herein.

The cyclooctane fuel produced from the method herein has the following structure:

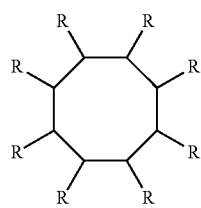

(III)

where each R is independently a hydrogen or an alkyl group. Some specific examples of the alkyl cyclooctane fuel produced include 1,4-dimethylcyclooctane (1,4-DMCO), 1,5-dimethylcyclooctane, 1,4-diethylcyclooctane, 1,4-dipropylcyclooctane, methylcyclooctane, and combinations of alkyl cyclooctane fuels. In some examples, the fuel produced is a jet fuel with hydrocarbons having molecular weights ranging from about 112 g/mol to about 224 g/mol and carbon atoms ranging from about 8 carbons to about 16 carbons. In other examples, the fuel produced is a diesel fuel with hydrocarbons having molecular weights ranging from about 112 g/mol to about 308 g/mol and carbon atoms ranging from about 8 carbons to about 22 carbons. An example of step 104 is shown in FIG. 2. 1,6-dimethyl-1,4-cyclooctadiene (DMCOD) is hydrogenated to produce 1,4-dimethylcyclooctane (1,4-DMCO).

In another example, the fuel produced using the method described herein can be used as a blendstock to be mixed with other fuels. The other fuel may be any type of fuel, such as biofuels or petroleum-based fuels. In particular, some examples of biofuels include HEFA-JET, Fischer-Tropsch, ATJ fuels, direct sugar to hydrocarbon (DSHC) fuels, and combinations thereof. Some examples of petroleum-based fuels include JP-8, JP-5, Jet-A, Jet-A1, F-24, Diesel #2, F-76, and combinations thereof. In an example, the cyclooctane fuel may be blended in an amount ranging from about 1% v/v to about 99% v/v based on the total v/v of the blended fuel. In an example, if the cyclooctane fuel is blended as a jet fuel, the cyclooctane fuel may be blended in an amount ranging from about 1% v/v to about 50% v/v based on the total v/v of the jet fuel.

To further illustrate the present disclosure, examples are given herein. These examples are provided for illustrative purposes and are not to be construed as limiting the scope of the present disclosure.

Examples

All air and moisture-sensitive manipulations were performed using Schlenk techniques on a dual manifold vacuum line under ultra-high purity argon, or in an inert atmosphere glove box under purified nitrogen. $^1$H NMR and $^{13}$C{$^1$H} NMR spectra were recorded using either a Bruker Avance 300 or 500 MHz spectrometer and spectra are referenced to the residual solvent peaks. Products were further characterized via GC-MS. The GC-MS system was equipped with an RTX-5MS 30-meter column and the analysis was conducted under the following conditions: inlet temperature, 250° C.; initial column temperature, 40° C.; temperature ramp, 4° C./min to 100° C.; $2^{nd}$ temperature ramp, 20° C./min to 300° C.

Example 1: [($^{Me}$PI)FeCl(μ-Cl)]$_2$ Pre-catalyst Synthesis

Figure 3:
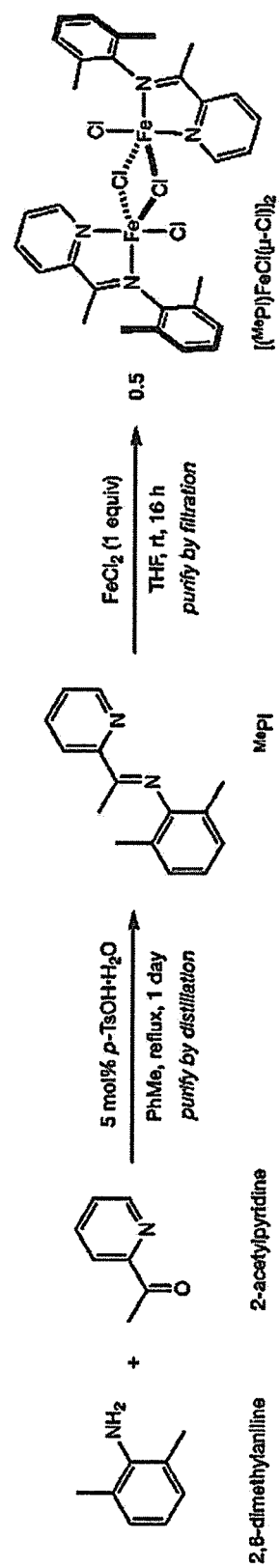
FIG. 3 is a scheme illustrating an example of a method for making the catalyst used in the method for making a fuel described herein.

The procedure for the synthesis of the iron pre-catalyst [($^{Me}$PI)FeCl(μ-Cl)]$_2$ is shown in FIG. 3. The ligand $^{Me}$PI, where $^{Me}$PI=N-(2,6-dimethylphenyl)-1-(pyridin-2-yl)ethan-1-imine, was first prepared. The synthesis was conducted in an N$_2$ atmosphere glovebox. In the glovebox, a 20-mL scintillation vial was charged with $^{Me}$PI (1.5 mmol, 1.0 equiv), iron(II) chloride (1.5 mmol, 1.0 equiv), and a PTFE-coated magnetic stir bar. Tetrahydrofuran (15 mL) was added, and the vial was sealed with a PTFE-lined screw cap. The reaction mixture was maintained with vigorous stirring at ambient temperature (~23° C.). After 16 hours, the solvent was removed in vacuum. The solid was resuspended in diethyl ether (15 mL) and collected by vacuum filtration over a glass frit, rinsing with additional diethyl ether (3-20×5 mL) until the rinses ran clear and the isolated solid was a uniform lavender color.

Sample uniformity was assayed by elemental analysis and zero-field Mößbauer spectroscopic analysis of samples in the solid state at 80 K. Elemental Analysis: for $C_{30}H_{32}Cl_4Fe_2N_4$, Calculated: C, 51.32%; H, 4.59%; N, 7.98%. Found: C, 51.35%; H, 4.61%; N, 7.94%. Zero-Field $^{57}$Fe Mößbauer Spectroscopy (solid-state, 80 K): δ=1.09 mm/s, |ΔE$_Q$|=3.47 mm/s.

Example 2: [4+4]-Cyclodimerization of Isoprene

In an N$_2$ atmosphere glovebox, an oven-dried 500-mL round-bottom Schlenk flask was charged with [($^{Me}$PI)FeCl(μ-Cl)]2 (0.175 g, 0.25 mmol, 0.025 mol % [Fe]), a large football-shaped stir bar, and isoprene (10 g, 0.15 mol). A separate, oven-dried 250-mL round-bottom flask was charged with additional isoprene (126 g, 1.85 mol; to a total of 2.0 mol, 1.0 equiv). Both flasks were sealed with virgin rubber septa and removed from the glovebox. The Schlenk flask side-arm was fit with an Ar-inlet hose, and the hose was evacuated and back-filled with Ar three times before the stopcock was opened, placing the flask under a positive pressure of Ar.

The Schlenk flask was then lowered into a cold-water bath (10° C. to 15° C.; maintained with ice chips), and stirring was initiated. While stirring vigorously under Ar, the catalyst was activated with the addition of MeMgCl solution (3M in THF, 0.4 mL, 1.2 mmol, 0.06 mol %) injected through the septum. The reaction was maintained for 10 minutes as the mixture changed colors from purple to green to blue-green. After 10 minutes, the flask containing the remaining isoprene was placed under a positive pressure of Ar. An oven-dried stainless-steel cannula was connected between the two flasks, and the Schlenk flask was fit with an N$_2$-flushed, but unpressurized balloon. The stopcock on the Schlenk flask side-arm was closed, and the isoprene was added over the span of 20 minutes by an Ar-driven cannula transfer, releasing pressure into the balloon.

Figure 4:
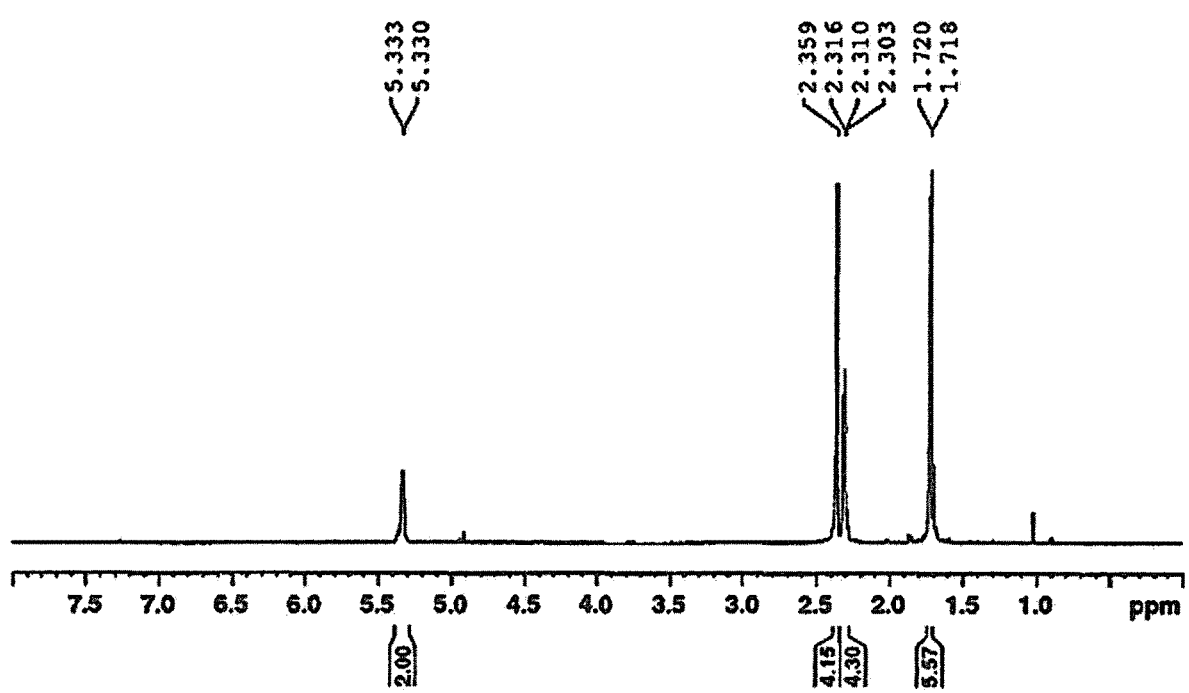
FIG. 4 is a $^1$H NMR spectrum of a cyclooctadiene example produced during the first step of the method for making a fuel described herein.
Figure 5:
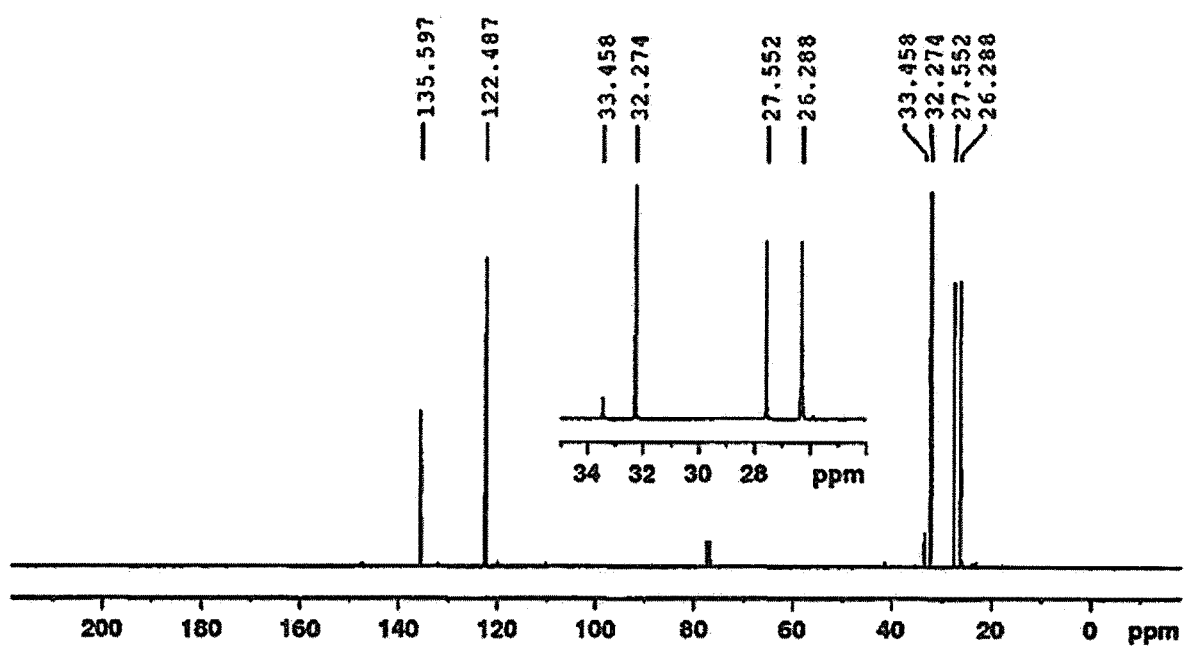
FIG. 5 is a $^{13}$C NMR spectrum of a cyclooctadiene example produced during the first step of the method for making a fuel described herein.

After the addition was complete, the stopcock was reopened, and the cannula and needle were removed. The puncture marks in the septum were covered with grease and PTFE-tape. The reaction was maintained with stirring under gentle Ar pressure for 24 hours, and the water bath was allowed to warm gradually to ambient temperature (~23° C.). After 24 hours, the reaction vessel was then opened to air, and 1,6-dimethyl-1,5-cyclooctadiene was isolated (92% conversion; 97% [4+4]; 91:9 r.r) by vacuum distillation directly from the reaction vessel. FIG. 4 shows a $^1$H NMR spectrum of the product. $^1$H NMR (500 MHz, CDCl$_3$): δ 5.33 (bs, 2H, =CH—), 2.36 (s, 4H, CH$_2$), 2.34-2.29 (m, 4H, CH$_2$), 1.72 (s, 6H, CH$_3$). FIG. 5 shows a $^{13}$C spectrum of the product. $^{13}$C{$^1$H} NMR (75.5 MHz, CDCl$_3$): δ 135.6 (=C (CH$_3$)—), 122.5 (=CH—), 32.3 (CH$_3$), 27.6 (CH$_2$), 26.3 (CH$_2$). The NMR spectra confirmed the product isolated for this example was primarily 1,6-dimethyl-1,5-cyclooctadiene where a ratio of 1,6-dimethyl-1,5-cyclooctadiene to 1,5-dimethyl-1,5-cyclooctadiene is 10:1.

In a second example of the [4+4]-cyclodimerization of isoprene, in an M.Braun glovebox with an atmosphere of purified $N_2$, an oven-dried 50-mL round bottom flask was charged with [($^{Me}$PI)FeCl(μ-Cl)]$_2$ (0.035 g, 0.05 mmol dimer, 0.1 mmol [Fe], 0.05 mol % [Fe]), isoprene (1.0 g, 15 mmol), and an oven-dried PTFE-coated magnetic stir bar. The reaction was initiated with the addition of MeMgCl (3 M in THF, 0.080 mL, 0.24 mmol, 0.12 mol %). The reaction flask was covered with a vacuum-dried rubber septum or an oven-dried ground-glass stopper. The reaction mixture was stirred vigorously in the glovebox for 10 minutes or until a deep teal color persisted. Additional isoprene (12.6 g, 185 mmol; to a total of 200 mmol, 1.0 equiv) was then added in the glovebox. The reaction flask was sealed, and the reaction mixture was maintained with vigorous stirring at ambient temperature (~23° C.).

Aliquots (50 uL) of the reaction mixture were removed regularly by syringe to monitor for conversion. For each aliquot, the sample was removed from the glovebox, diluted with $CDCl_3$ (0.7 mL), filtered through a plug of Celite, and analyzed by $^1$H NMR spectroscopy (500 MHz, $CDCl_3$, 25° C.). Complete consumption of isoprene (>98% conversion) was observed after a 19.5 hour reaction time. Upon complete consumption of isoprene, the reaction flask was removed from the glovebox and opened to air in a fume-hood. The flask was fitted with an oven-dried short-path distillation head, which was connected to a high vacuum manifold. The product mixture was isolated by vacuum distillation into a tared, 50- or 100-mL receiving flask cooled by dry ice/acetone. Vacuum distillation afforded a 1,6-dimethyl-1,5-cyclooctadiene and 1,5-dimethyl-1,5-cyclooctadiene product mixture (a 10:1 ratio) as a colorless liquid (12.880 g, 94.5 mmol, 95% isolated yield, 97% [4+4], 91:9 r.r.).

In a third example, the [4+4]-cyclodimerization of isoprene was conducted as previously described herein in reference to the second example above. Complete consumption of isoprene (>98% conversion) was observed after a 23 hour reaction time. Upon complete consumption of isoprene, the reaction flask was removed from the glovebox and opened to air in a fume-hood. The flask was fitted with an oven-dried short-path distillation head, which was connected to a high vacuum manifold. The product mixture was isolated by vacuum distillation into a tared, 50- or 100-mL receiving flask cooled by dry ice/acetone. Vacuum distillation afforded a 1,6-dimethyl-1,5-cyclooctadiene and 1,5-dimethyl-1,5-cyclooctadiene product mixture (a 10:1 ratio) as a colorless liquid (12.353 g, 90.7 mmol, 91% isolated yield, 97% [4+4], 91:9 r.r.).

In a fourth example, the [4+4]-cyclodimerization of isoprene was conducted as previously described herein in reference to the second example above. Complete consumption of isoprene (>98% conversion) was observed after a 21 hour reaction time. Upon complete consumption of isoprene, the reaction flask was removed from the glovebox and opened to air in a fume-hood. The flask was fitted with an oven-dried short-path distillation head, which was connected to a high vacuum manifold. The product mixture was isolated by vacuum distillation into a tared, 50- or 100-mL receiving flask cooled by dry ice/acetone. Vacuum distillation afforded a 1,6-dimethyl-1,5-cyclooctadiene and 1,5-dimethyl-1,5-cyclooctadiene product mixture (a 10:1 ratio) as a colorless liquid (12.213 g, 89.6 mmol, 90% isolated yield, 96% [4+4], 90:10 r.r.).

In a fifth example, the [4+4]-cyclodimerization of isoprene was conducted as previously described herein in reference to the second example above. Complete consumption of isoprene (>98% conversion) was observed after a 14 hour reaction time. Upon complete consumption of isoprene, the reaction flask was removed from the glovebox and opened to air in a fume-hood. The flask was fitted with an oven-dried short-path distillation head, which was connected to a high vacuum manifold. The product mixture was isolated by vacuum distillation into a tared, 50- or 100-mL receiving flask cooled by dry ice/acetone. Vacuum distillation afforded a 1,6-dimethyl-1,5-cyclooctadiene and 1,5-dimethyl-1,5-cyclooctadiene product mixture (a 10:1 ratio) as a colorless liquid (12.659 g, 92.9 mmol, 93% isolated yield, 96% [4+4], 91:9 r.r.).

Example 3: Single-Component Organometallic Pre-Catalyst

Figure 6:
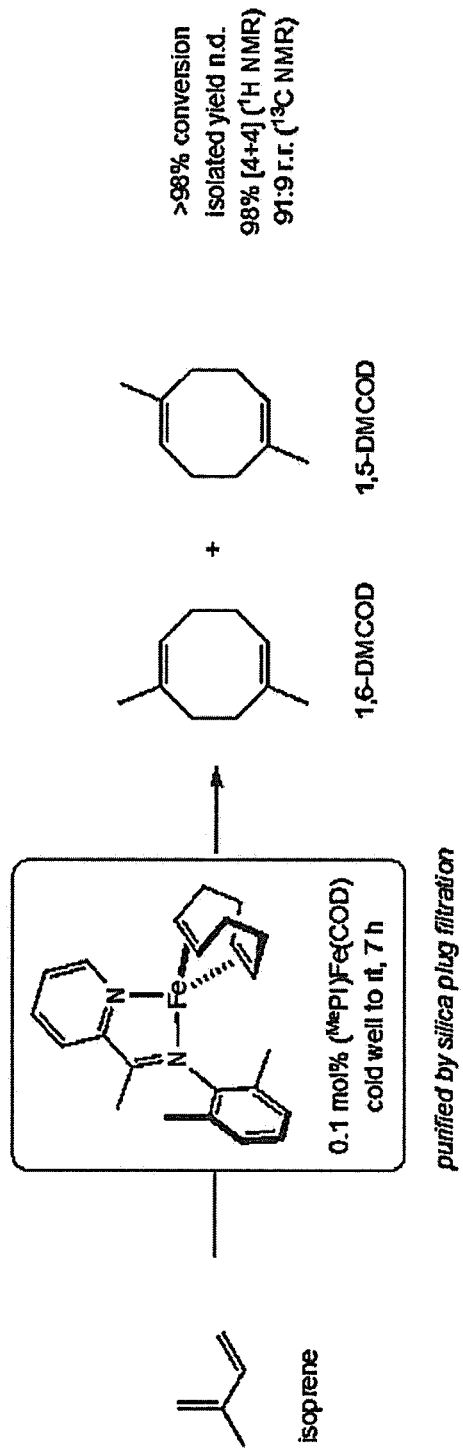
FIG. 6 is a scheme illustrating an example of the method for making a cyclooctadiene produced during the first step of the method for making a fuel described herein.

An example of [4+4]-cyclodimerization of isoprene using a single-component iron pre-catalyst is shown in FIG. 6. As shown in FIG. 6, the single-component iron pre-catalyst is ($^{Me}$PI)Fe(COD). In an M.Braun glovebox with an atmosphere of purified $N_2$, an oven-dried 20-mL scintillation vial was charged with isoprene (0.50 g, 7.3 mmol), cyclooctane (0.033 g, 0.30 mmol; added as an internal standard), and an oven-dried PTFE-coated magnetic stir bar. The vial was sealed with a PTFE-lined screw cap and chilled in a liquid $N_2$-cooled cold well. After 30 minutes, the vial was removed from the cold well and positioned on a stir plate; the reaction was initiated with the addition of ($^{Me}$PI)FeCl(COD) (0.003 g, 0.007 mmol [Fe], 0.1 mol % [Fe]) as a solid. The reaction vial was sealed, and the reaction mixture was maintained with vigorous stirring as it gradually warmed to ambient temperature (~23° C.). After 7 hours, the reaction vessel was removed from the glovebox and opened to air. The crude material was filtered through a plug of silica, eluting with pentane. The filtrate was concentrated in vacuum to afford a 1,6-dimethyl-1,5-cyclooctadiene and 1,5-dimethyl-1,5-cyclooctadiene product mixture (a 10:1 ratio) as a colorless liquid (>98% conversion, isolated yield not determined, 98% [4+4], 91:9 r.r.).

Example 4: Single-Component Pre-catalysts and In Situ Activation

Figure 7:
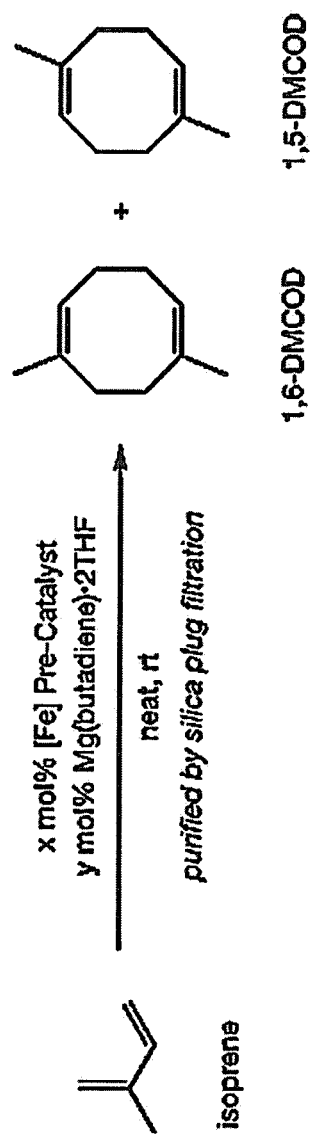
FIG. 7 is a scheme illustrating another example of the method for making a cyclooctadiene produced during the first step of the method for making a fuel described herein.

FIG. 7 shows an example of in situ activation of a single-component pre-catalyst. As shown in FIG. 7, In an M.Braun glovebox with an atmosphere of purified $N_2$, four oven-dried 1.5-mL scintillation vials were each charged with the indicated iron pre-catalyst (0.01 mmol, 1 mol % [Fe]), Mg(butadiene)·2THF (0.003 g, 0.01 mmol, 1 mol %; added only when using [($^{Me}$PI)FeCl(μ-Cl)]$_2$), cyclooctane (0.010 g, 0.089 mmol; added as an internal standard), and an oven-dried PTFE-coated magnetic stir bar. The reactions were initiated with the addition of isoprene (100 μL, 1.0 mmol) using a μL syringe. The reaction vials were sealed with PTFE-lined screw caps and maintained with vigorous stirring at ambient temperature (23° C.). Aliquots (<2 μL) of the reaction mixtures were removed regularly by capillary to monitor for conversion. For each aliquot, the sample diluted with $Et_2O$, filtered through a plug of lint-free laboratory wipe, removed from the glovebox, and analyzed by gas chromatography.

After 24 hours, the vials were removed from the glovebox and opened to air. The crude material from each reaction was filtered through a plug of silica, eluting with pentane. The filtrate was concentrated in vacuum to afford a 1,6-dimethyl-1,5-cyclooctadiene and 1,5-dimethyl-1,5-cyclooctadiene product mixture (a 10:1 ratio) as a colorless liquid. The results at each time point are summarized in Table 1 below.

TABLE 1

[4 + 4]-cyclodimerization results.

| Entry | [Fe] Pre-Catalyst | x (mol %) | y (mol %) | 1 hour: yield | 1 hour: % [4 + 4] | 4 hours: yield | 4 hours: % [4 + 4] | 24 hours: yield | 24 hours: % [4 + 4] | r.r. |
|---|---|---|---|---|---|---|---|---|---|---|
| 1 | [($^{Me}$PI)FeCl(μ-Cl)]$_2$ | 0.5 | 1 | 99% | 96% | 95% | 96% | 97% | 96% | 92:8 |
| 2 | ($^{Me}$PI)Fe(COD) | 1 | 0 | 98% | 96% | 94% | 96% | 92% | 96% | 90:10 |
| 3 | ($^{Me}$PI)Fe(M$^{vi}$M$^{vi}$) | 1 | 0 | 93% | 96% | 94% | 96% | 96% | 96% | 90:10 |
| 4 | ($^{Mes}$PI)$_2$Fe | 1 | 0 | <1% | n.d. | 6% | >90% | 34% | 96% | 92:8 |

Example 5: Synthesis of 1,4-Dimethylcyclooctane

A 2.0 L reinforced glass bomb was charged with 1,6-dimethyl-1,5-cyclooctadiene (220 g, 1.62 mol), platinum (IV) oxide hydrate (2.05 g), and acetic acid (50 mL). The flask was sealed with a rubber septa and the headspace was filled with nitrogen. The vessel was then evacuated and placed within a Parr hydrogenation apparatus. The flask was charged with hydrogen, evacuated under vacuum, and recharged with hydrogen four times. The vessel was finally charged with hydrogen (50 psi) and vigorously shaken for the remainder of the reaction. The vessel was recharged with hydrogen multiple times to a maximum pressure of 50 psi until rapid consumption was complete. The flask was then recharged with hydrogen and shaken overnight.

Figure 8:
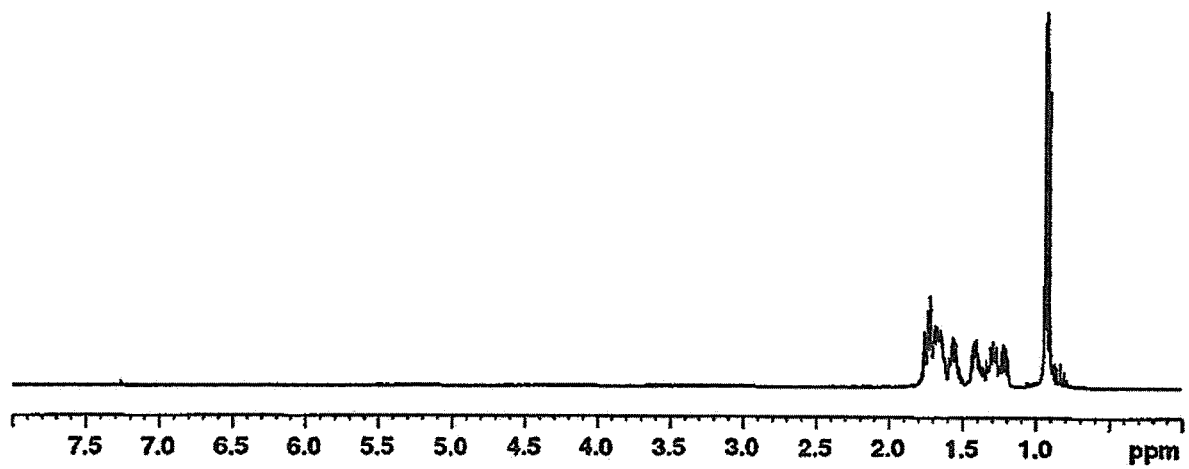
FIG. 8 is a $^1$H NMR spectrum of a cyclooctane fuel example produced using the method for making a fuel described herein.
Figure 9:
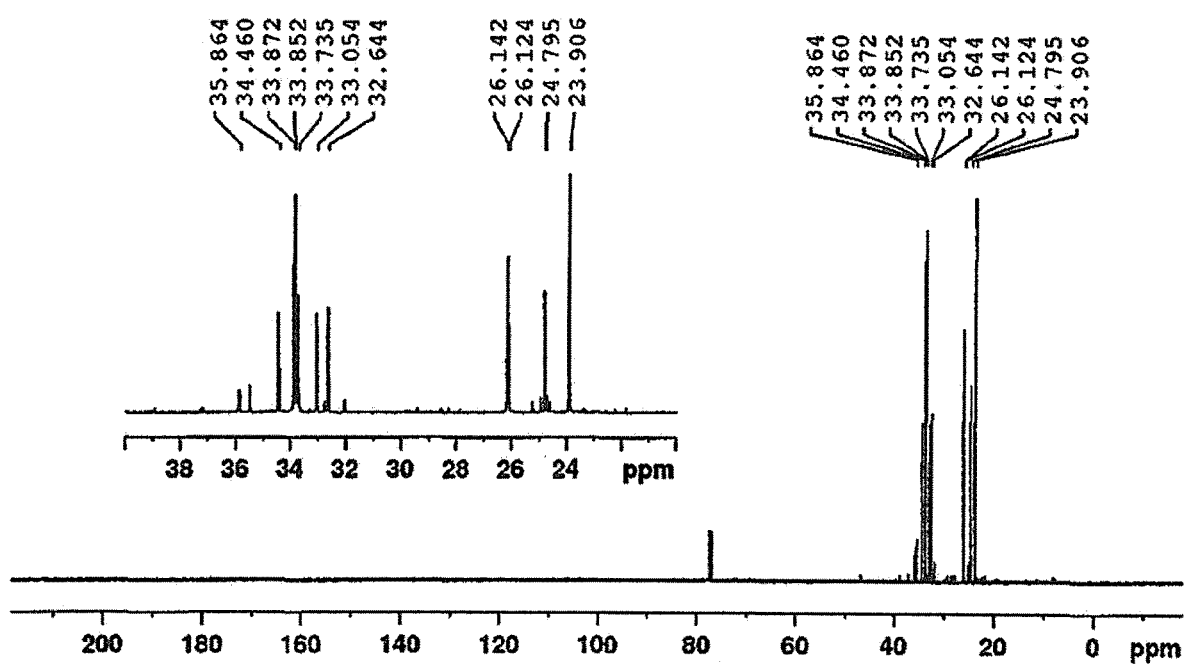
FIG. 9 is a $^{13}$C NMR spectrum of a cyclooctane fuel example produced using the method for making a fuel described herein.

The vessel was then evacuated, removed from the hydrogenation apparatus, and quickly put under nitrogen. The contents were filtered through Celite and washed with pentane. The filtrate was transferred to a separatory funnel and washed with DI water (300 mL), saturated sodium bicarbonate solution (300 mL), and lastly, additional DI water (300 mL). The organic layer was collected and dried with magnesium sulfate, filtered, and the volatiles were carefully removed on a rotary evaporator to give a pale yellow solution. The crude product was then distilled under high vacuum (~0.01 Torr). The first fraction, which distilled at room temperature, consisted of residual pentane and some of the product. The temperature was then increased and a second fraction was collected between 25° C. and 40° C. to yield a colorless, low viscosity liquid (192.06 g, 85% yield). Anal. Calc for $C_{10}H_2O$: C, 85.63; H, 14.37. Found: C, 85.48; H, 14.54. FIG. 8 shows a H NMR spectrum of the product. $^1$H NMR (500 MHz, CDCl$_3$): δ 1.76-1.21 (m, 14H), 0.939-0.906 (CH$_3$). FIG. 9 shows a $^{13}$C NMR spectrum of the product. $^{13}$C{$^1$H} NMR (75.5 MHz, CDCl$_3$): δ 34.4, 33.87, 33.85, 33.7, 33.1, 32.6, 26.14, 26.12, 24.8, 23.9. The NMR spectra confirmed the product isolated for this example was primarily 1,4-dimethylcyclooctane (DMCO).

Example 6: 1,4-Dimethylcyclooctane Properties

The kinematic viscosity and density of DMCO were measured with a Stabinger Viscometer, SVM 3001, connected to a TC-502 circulation cooler. A 5 mL disposable syringe was used to inject the sample into the viscometer. To determine the flash point, samples were analyzed with a Grabner Instruments/Ametek Miniflash FLP Touch according to ASTM D7094. For each measurement, 2 mL of fuel were transferred via auto pipette to a 7 mL stainless steel sample cup. The initial temperature of each run was set to 28° C. and the final temperature was set to 64° C. The freezing point was evaluated by placing a sample of the fuel in a dry ice/acetone bath for up to one hour. Additionally, the net heat of combustion (NHOC) measurements were conducted using ASTM D240N.

Figure 10:
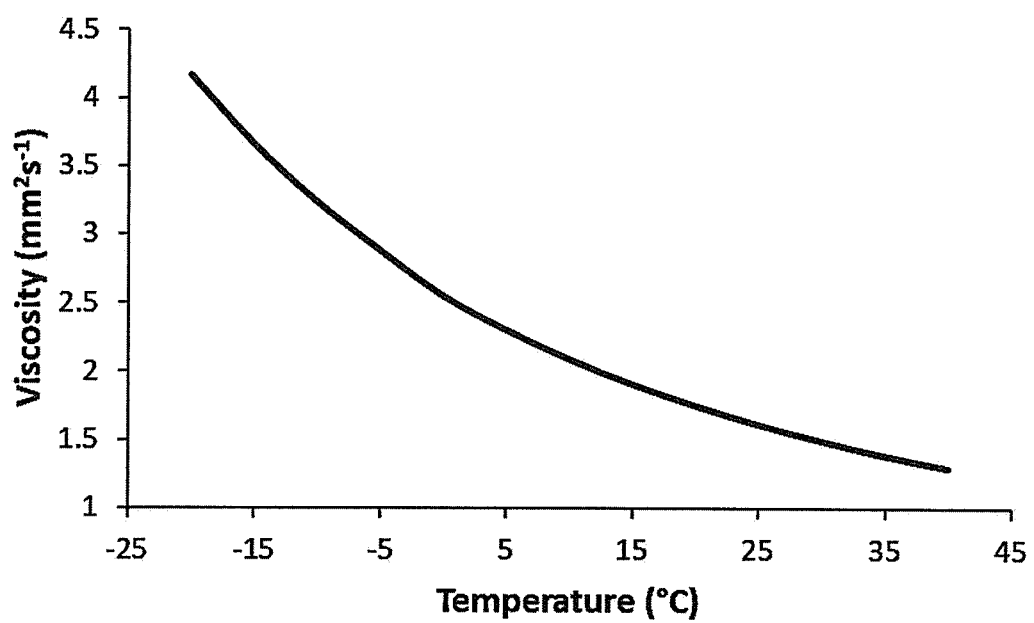
FIG. 10 is a graph of the Temperature (X-axis, labeled "Temperature (° C.)") vs. the Viscosity (Y-axis, labeled "Viscosity (mm$^2$s$^{-1}$)") for a cyclooctane fuel example described herein.

The kinematic viscosity of 1,4-dimethylcyclooctane was measured at temperatures ranging from −20° C. to 40° C. FIG. 10 shows a plot of these results at each temperature. The measured kinematic viscosity was significantly lower compared to the specification for conventional jet fuel (e.g., Jet-A, Jet-A1, JP-5, F-24, or JP-8 fuel etc.) shown in Table 2. The results indicate that the fuel produced herein can be blended with nearly all types of jet fuel in any proportion to reduce viscosity and improve fuel performance relative to conventional jet fuel. The lower viscosity also indicates that blending 1,4-dimethylcyclooctane with conventional jet fuel will improve combustion efficiency and reduce soot production.

In addition to viscosity data, Table 2 below shows other key fuel properties of 1,4-dimethylcyclooctane produced using the method herein, and those properties for conventional jet fuel. As shown in Table 2, 1,4-dimethylcyclooctane has a higher gravimetric net heat of combustion (NHOC) and volumetric NHOC compared to conventional jet fuel. In addition, the density and flash point are higher, and the kinematic viscosity and freezing point are both lower, than conventional jet fuel. As a result, the use of 1,4-dimethylcyclooctane can improve aircraft performance compared to conventional jet fuels. Furthermore, using cycloparaffins to replace aromatic compounds in conventional or bio-based fuels reduces soot formation, and therefore, reduces long-term maintenance costs for airplanes.

TABLE 2

Fuel Properties of Example Fuel and Conventional Jet Fuels.

| Property | 1,4-dimethylcyclooctane | Jet-A1/JP-8 Fuel |
|---|---|---|
| Gravimetric NHOC | 43.822 MJ/kg | >42.8 MJ/kg |
| Volumetric NHOC | 36.222 MJ/L | >33.17 MJ/L |
| Density | 0.827 g/mL | >0.775 g/mL |
| Kinematic Viscosity (−20° C.) | 4.17 mm$^2$s$^{-1}$ | >8.0 mm$^2$s$^{-1}$ |
| Freezing Point | <−78 C. | >−47° C. |
| Flash Point | 50° C. | >38° C. |

Example 7: 1,4-Dimethylcyclooctane Blends

To evaluate the 1,4-dimethylcyclooctane fuel produced herein as a blendstock, 1,4-dimethylcyclooctane was mixed with jet fuel range hydroprocessed esters and fatty acid fuel (HEFA-JET). Four different blends of 1,4-dimethylcyclooctane were prepared ranging from about 20% v/v to about 50% v/v of 1,4-dimethylcyclooctane. In addition, 100% HEFA was tested for comparison. The density, kinematic viscosity at −40° C., kinematic viscosity at −20° C., and the gravimetric NHOC were all tested as previously described herein. The results are shown below in Table 3.

TABLE 3

Fuel Properties of HEFA-Jet and 1,4-dimethylcyclooctane blends.

| Fuel | Density (15° C., g/mL) | Viscosity, (−40° C., mm²s⁻¹) | Viscosity (−20° C., mm²s⁻¹) | NHOC (MJ/kg) |
|---|---|---|---|---|
| HEFA | 0.762 | 12.77 | 5.65 | 43.73 |
| 20% DMCO | 0.773 | 11.26 | 5.25 | 43.75 |
| 30% DMCO | 0.780 | 10.54 | 5.03 | 43.76 |
| 40% DMCO | 0.788 | 9.93 | 4.84 | 43.77 |
| 50% DMCO | 0.793 | 9.43 | 4.68 | 43.78 |

The blendstocks between 30% v/v and 50% v/v of 1,4-dimethylcyclooctane provide a fuel with a density that meets the Jet-A1/JP-8 specifications, and exhibit an increase in density compared to HEFA. In addition, all of the blendstocks have a viscosity at −20° C. and −40° C. within the Jet-A1/JP-8 specifications and a decrease in viscosity compared to HEFA. In particular, the viscosity is below 12 mm²s⁻¹ in all fuel blends tested at −40° C., which reduces the risk of the fuel failing to relight at −40° C. The gravimetric NHOC was consistent in the blendstocks compared to HEFA due to the similar gravimetric NHOCs between HEFA and 1,4-dimethylcyclooctane.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless otherwise stated, any feature described herein can be combined with any aspect or any other feature described herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 1 atm to about 500 atm should be interpreted to include not only the explicitly recited limits of from about 1 to about 500 atm, but also to include individual values, such as 30 atm, 175 atm, 350 atm, etc., and sub-ranges, such as from about 50 atm to about 150 atm, etc.

In describing and claiming the examples disclosed herein, the singular forms "a", "an", and "the" include plural referents unless the context clearly dictates otherwise.

What is claimed is:

1. A method for making a cyclooctane fuel, comprising: reacting a conjugated diene or a mixture of conjugated dienes with a catalyst selected from the group consisting of a low valent iron catalyst stabilized with a pyridineimine ligand, an iron precatalyst coordinated to the pyridineimine ligand that is activated with a reducing agent, a low oxidation state Fe complex stabilized with a pyridineimine ligand and a coordinating ligand, and combinations thereof, thereby forming a cyclooctadiene with a structure of:

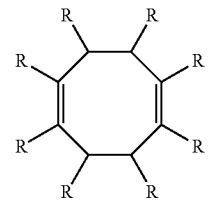

wherein each R is independently a hydrogen atom or an alkyl group;
hydrogenating the cyclooctadiene, thereby making the cyclooctane fuel with the structure of:

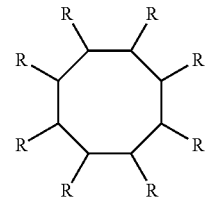

wherein each R is independently a hydrogen atom or an alkyl group.

2. The method of claim 1, wherein the conjugated diene or mixture of conjugated dienes include a number of carbons ranging from about 4 carbons to about 20 carbons.

3. The method of claim 1, wherein the pyridineimine ligand is selected from the group consisting of N-(2,6-dimethylphenyl)-1-(pyridin-2-yl)ethan-1-imine, N-(2,6-diethylphenyl)-1-(pyridin-2-yl)ethan-1-imine, N-(2,6-diisopropylphenyl)-1-(pyridin-2-yl)ethan-1-imine, N-(2,4,6-triimethylphenyl)-1-(pyridin-2-yl)ethan-1-imine, and combinations thereof.

4. The method of claim 3, wherein the catalyst is heterogeneous and is bound to a support material, wherein the support material is an inorganic or polymeric material.

5. The method of claim 4, wherein the catalyst is separated by filtration and reused in a subsequent reaction.

6. The method of claim 1, wherein the precatalyst is [(RPI)FeX$_2$]$_n$, wherein RPI is a pyridineimine ligand, X is Cl, Br, or I, n is 1 or 2, and the reducing agent is MeMgCl, Mg(C$_4$H$_6$)-THF, Mg(0), Mn(0), or NaBHEt$_3$.

7. The method of claim 1, wherein the reaction is conducted using the conjugated diene or mixture of conjugated dienes as both a solvent and a reactant.

8. The method of claim 1, wherein the hydrogenating occurs at a pressure ranging from about 1 atm to about 500 atm.

9. The method of claim 1, wherein the hydrogenating occurs at a temperature ranging from about 20° C. to about 200° C.

10. The method of claim 1, wherein the hydrogenating occurs in a polar solvent selected from the group consisting of acetic acid, methanol, ethanol, and combinations thereof.

11. The method of claim 1, wherein the hydrogenating uses i) a homogenous catalyst based on Fe or Ni or ii) a heterogeneous based catalyst based on Ni, Pd, Pt, or Ru.

12. The method of claim 1, wherein the cyclooctane fuel has hydrocarbons with molecular weights ranging from about 112 g/mol to about 224 g/mol and carbon atoms ranging from about 8 carbon atoms to about 16 carbon atoms.

13. The method of claim 1, wherein the cyclooctane fuel has hydrocarbons with molecular weights ranging from about 112 g/mol to about 308 g/mol and carbon atoms ranging from about 8 carbon atoms to about 22 carbons atoms.

14. The method of claim 1, further including mixing the cyclooctane fuel with a second fuel in an amount ranging from about 1% v/v to about 99% v/v based on the total v/v of the fuel, thereby forming a blended fuel.

15. The method of claim 14, wherein the blended fuel has a kinematic viscosity equal to or less than 12.00 $mm^2s^{-1}$ at temperatures equal to or greater than −40° C.

16. The method of claim 14, wherein the second fuel is selected from the group consisting of HEFA-Jet, Fischer-Tropsch Jet, ATJ, DSHC fuels, and combinations thereof.

17. The method of claim 14, wherein the second fuel is selected from the group consisting of JP-8, JP-5, Jet-A, Jet-A1, F-24, Diesel #2, F-76, and combinations thereof.

18. The method of claim 1, wherein the conjugated diene or mixture of conjugated dienes and the catalyst have a ratio of the conjugated diene or mixture of conjugated diene to the catalyst ranging from about 100:1 to about 1,000,000:1.

19. The method of claim 18, wherein the catalyst has a turnover number (TON) ranging from about 100 to about 1,000,000.

20. The method of claim 1, wherein the catalyst is homogeneous and the cyclooctane fuel is separated by low temperature vacuum distillation and the homogeneous catalyst is reused in a subsequent reaction.

* * * * *